United States Patent [19]

Vilkomerson

[11] Patent Number: 5,669,388
[45] Date of Patent: Sep. 23, 1997

[54] APPARATUS AND METHOD FOR AUTOMATIC PLACEMENT OF TRANSDUCER

[75] Inventor: David Vilkomerson, Princeton, N.J.

[73] Assignee: EchoCath, Inc., Monmouth Junction, N.J.

[21] Appl. No.: 699,228

[22] Filed: Aug. 19, 1996

Related U.S. Application Data

[60] Provisional application No. 60/003,293 Sep. 6, 1995.

[51] Int. Cl.$^6$ .................................................. A61B 8/00
[52] U.S. Cl. ............................................... 128/661.09
[58] Field of Search .................. 128/660.07, 660.08, 128/661.01, 661.08, 661.09, 661.1, 662.01; 73/861.25

[56] References Cited

U.S. PATENT DOCUMENTS

| | | |
|---|---|---|
| 5,105,813 | 4/1992 | Shikata .................. 128/661.09 |
| 5,375,600 | 12/1994 | Melton, Jr. et al. ............... 128/661.09 |
| 5,394,876 | 3/1995 | Ma ................................. 128/661.09 |
| 5,488,953 | 2/1996 | Vilkomerson . |
| 5,540,230 | 7/1996 | Vilkomerson . |

*Primary Examiner*—George Manuel
*Attorney, Agent, or Firm*—Plevy & Associates

[57] ABSTRACT

An apparatus and method is disclosed for locating a desired blood vessel within a predetermined volume of tissue. The apparatus and method includes a plurality of transducers which are operable to be positioned over the tissue. Each of the transducers when driven produces an output signal indicative of a characteristic of a blood vessel located under each transducer. A control system for selectively driving the transducers in order to produce a plurality of output signals and for comparing the plurality of output signals in order to determine the output signal having the largest amplitude which corresponds to the transducer positioned over the desired blood vessel.

21 Claims, 4 Drawing Sheets

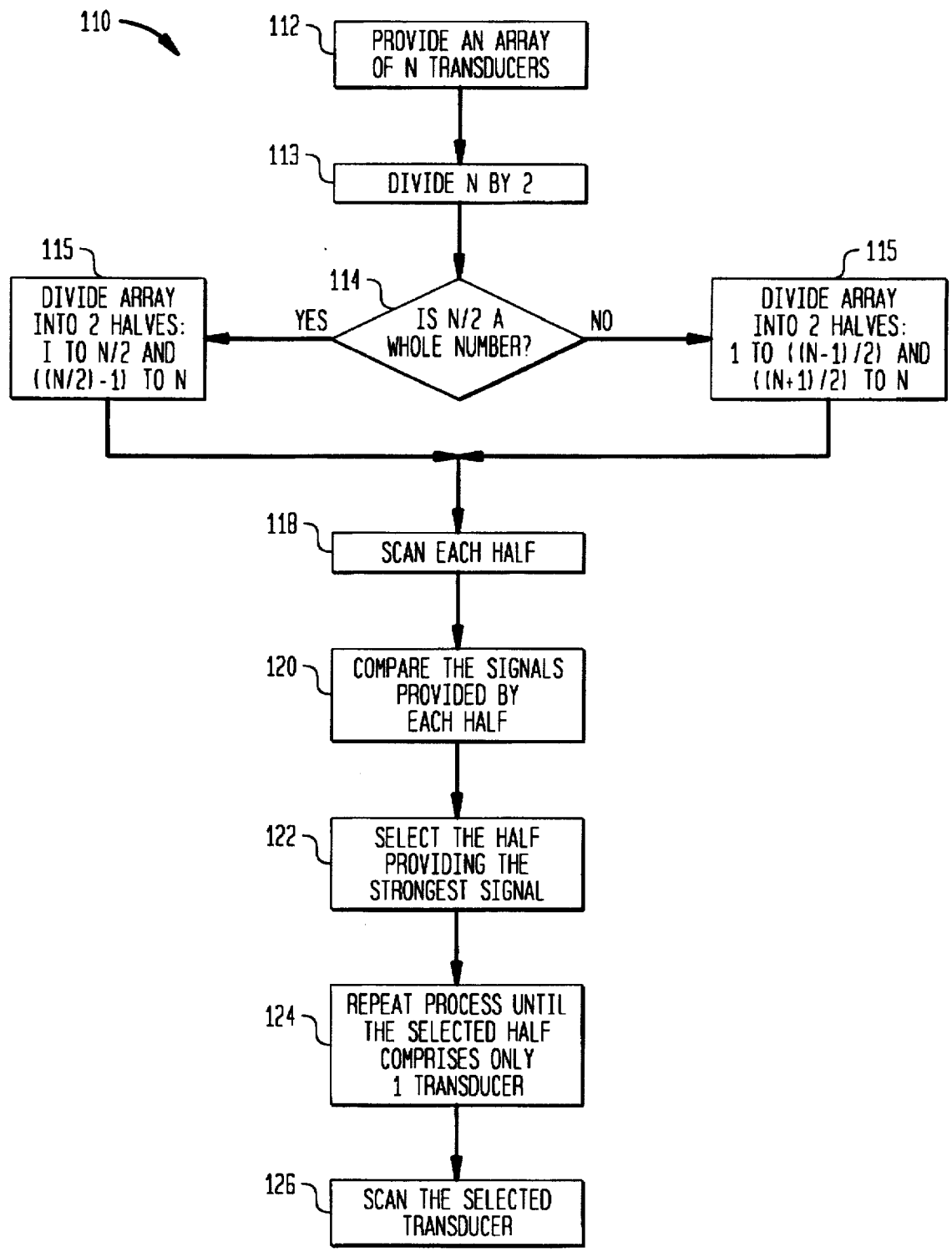

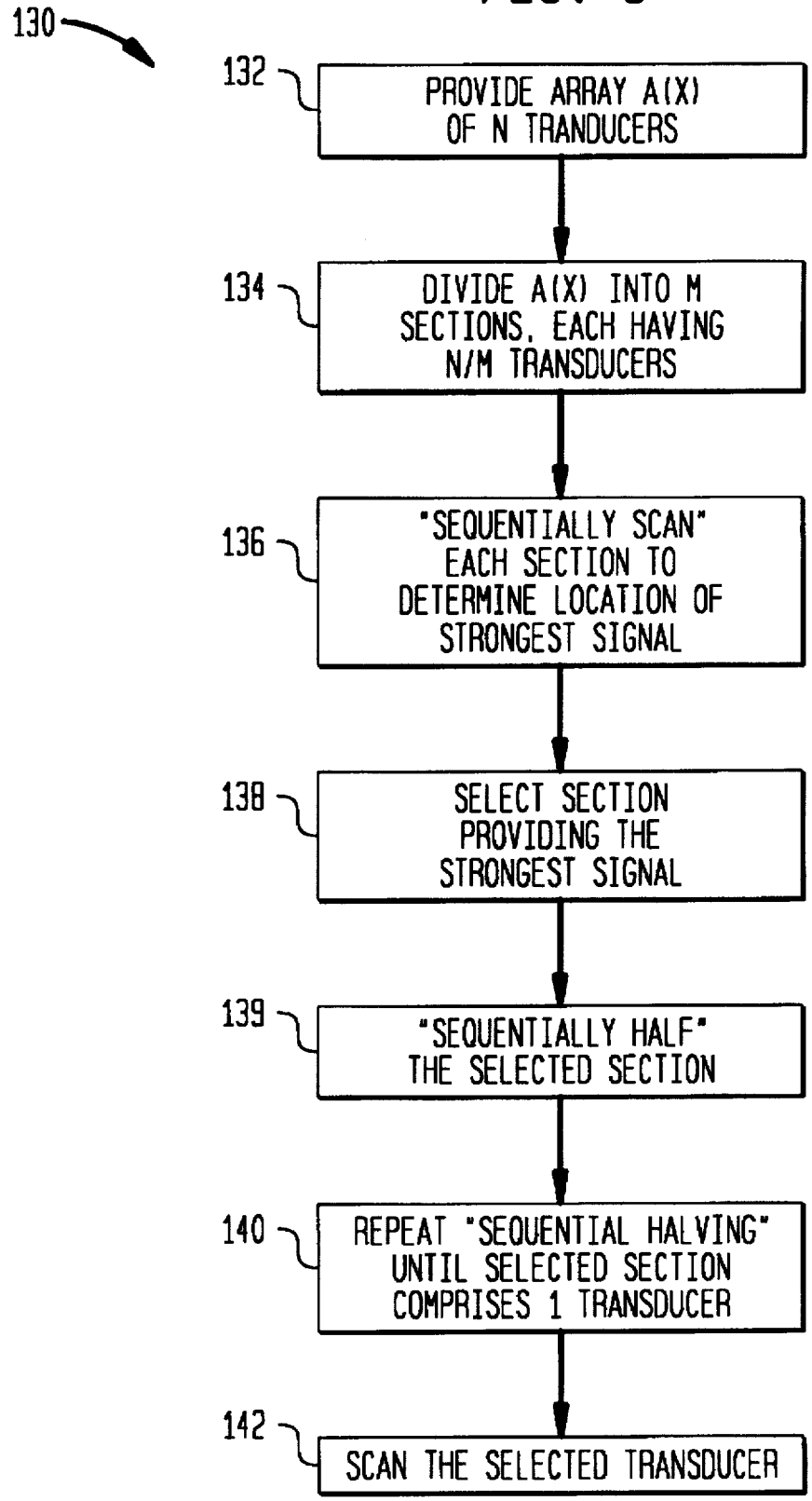

APPARATUS AND METHOD FOR AUTOMATIC PLACEMENT OF TRANSDUCER

Applicant hereby claims priority under 35 U.S.C. 119(e) for the present application based on a provisional application filed Sep. 6, 1995, entitled APPARATUS AND METHOD FOR AUTOMATIC PLACEMENT OF TRANSDUCER, Ser. No. 60/003,293, to the same inventor herein.

BACKGROUND OF THE INVENTION

1. Field of the Invention

The present invention relates generally to medical apparatuses and more particularly, to an apparatus and method for automatically locating a particular blood vessel within a patient by scanning a plurality of transducers over an area of the skin.

2. Description of the Prior Art

Measurement of blood flow is particularly important in emergency situations, such as on a battlefield or at an accident site. Several techniques are available for measuring blood flow in such situations. One such technique employs measurement of the signal provided by a transducer that is placed on the surface of the skin over a blood vessel. This technique is discussed in U.S. Pat. No. 5,540,230 to Vilkomerson, entitled DIFFRACTING DOPPLER-TRANSDUCER, issued on Jul. 30, 1996 and in U.S. Pat. No. 5,488,953 to Vilkomerson, entitled DIFFRACTING DOPPLER-TRANSDUCER, issued on Feb. 6, 1996. See also the article entitled "Diffractive Transducers for Angle-Independent Velocity Measurements", by David Vilkomerson, Proc. 1994 IEEE International Ultrasonics Symposium, pp. 1677–1682.

Such techniques of measuring blood flow initially require the user to locate a blood vessel for measurement, such as the carotid artery, the brachial arteries, or the radial arteries. However, if weak signals are provided at the selected location of the blood vessel, the measurements obtained may not be dependable. Accordingly, it is highly desirable to determine the location of the blood vessel providing the strongest signal.

FIG. 1 shows a conventional method of locating a blood vessel manually by scanning a transducer (not shown) across several positions 11–18 on the surface of the skin 19 until the position of the blood vessel 15 associated with the strongest signal is determined. However, since this method may be difficult and time consuming for emergency situations or dangerous in battlefield situations, manual scanning may be impractical.

Accordingly, it is the object of the present invention to substantially overcome or eliminate such disadvantages by providing an improved apparatus and method for quickly and automatically locating a blood vessel by scanning a plurality of transducers over an area of the skin to determine the location of the blood vessel associated with the strongest signal and for measuring the rate of blood flow through the located blood vessel.

SUMMARY OF THE INVENTION

An apparatus and method is disclosed for locating a desired blood vessel within a predetermined volume of tissue. The apparatus and method includes a plurality of transducers which are operable to be positioned over the tissue. Each of the transducers when driven produces an output signal indicative of blood flow in a vessel located under each transducer. A control means for selectively driving the transducers in order to produce a plurality of output signals and for comparing the plurality of output signals in order to determine the output signal having the largest amplitude which corresponds to the transducer positioned over the desired blood vessel.

BRIEF DESCRIPTION OF THE DRAWINGS

The foregoing and other objects, features, and advantages of the invention will be apparent from the following more particular description of the preferred embodiments of the invention, as illustrated in the accompanying drawings, wherein:

FIG. 5 is a schematic view of the "sequential halving" procedure of the present invention; and FIG. 6 is a schematic view of the "hybrid" procedure of the present invention.

DETAILED DESCRIPTION OF THE INVENTION

Figure 1:
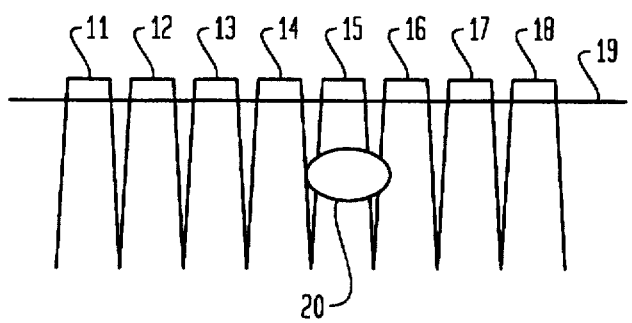
FIG. 1 is a schematic view of a prior art method for locating a blood vessel.
Figure 2:
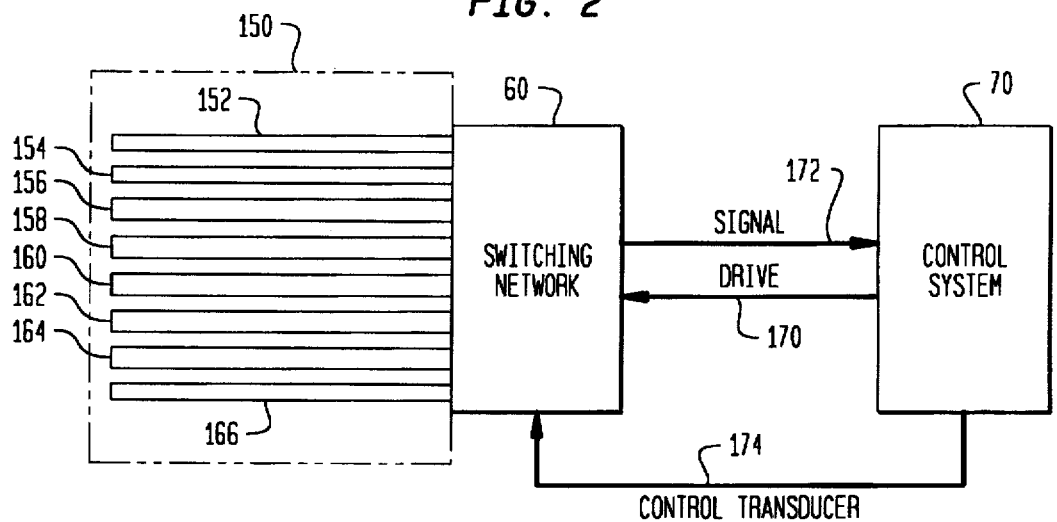
FIG. 2 is a schematic view of the apparatus of the present invention.

Referring to FIG. 2, the present invention comprises an array 150 of transducers which are coupled to a switching network 60 and are driven by a control system 70.

Specifically, the array 150 includes eight (8) transducers 152–166 which are of the type that measure various characteristics of a blood vessel via placement of the transducers on the surface of the skin over the blood vessel. An example of such transducers can be found in both U.S. Pat. No. 5,488,953 and U.S. Pat. No. 5,540,230. It should be understood, however, that non-diffractive Doppler transducers, as well as other transducers used with blood vessels, e.g. $PO_2$ type, equally fall within the scope of this invention. Further, since the transducers 152–166 are placed directly on the surface of the skin, each transducer 152–166 typically should have at least one flat surface for communicating with the skin surface.

Figure 3:
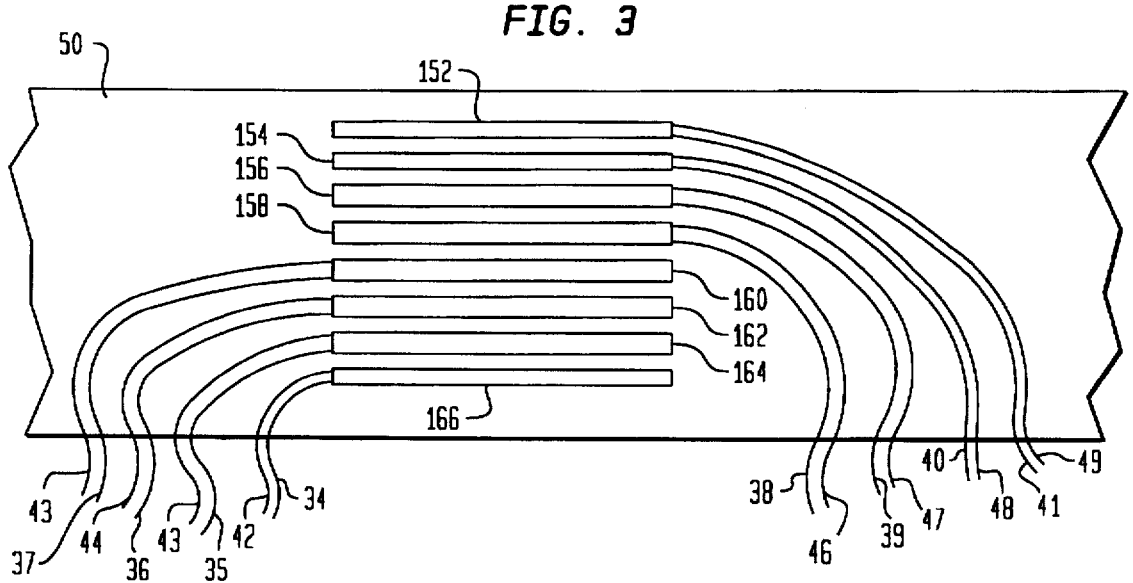
FIG. 3 is a plan view of the array of transducers shown in FIG. 2 secured to a flexible material.

Referring to the exemplary embodiment illustrated in FIG. 3, the eight (8) transducers 152–166 are shown secured to a flexible material 50, such as a bandage, length of gauze tape, or a BAND-AID®. It should be understood that the transducers 152–166 can be affixed to any material or substrate, providing that the material can be held in place on the surface of the skin.

The transducers 152–166 are arranged in a linear configuration and are uniformly spaced apart on the material 50 over a predetermined distance in order to scan over a predetermined scanning area. It should be understood that the distance between each of the transducers 152–166 can be varied. Further, the overall size of the scanning area (the distance between 152 and 166) can be increased or decreased by varying the number of transducers employed or by varying the spacing between the existing transducers 152–166. Finally, it should be understood that the transducers 152–166 can be arranged in other configurations, such as a matrix configuration.

The size and spacing of the transducers 152–166 in the array depends upon the blood vessel which flow is to be measured. As is known to one skilled in the art, the best signal-noise ratio is obtained when the transducer is approximately the same size as the vessel to be measured. The width of the array should be such that one of the transducers is substantially over the vessel, if landmarks for the vessel position are easily found. As for some vessels, the width of the array need not be large, as the approximate position of the vessel is well defined.

If landmarks for the vessel are not found or equivalently there is a large degree of variation in the position of the desired vessel with regard to anatomical marks, the array should be large enough to ensure that the approximate placement is substantially over the vessel. Knowledge of the size of the transducer and the total width of the array determines the number of transducers and their placement.

Referring to FIGS. 2 and 3, each of the transducers 152–166 of the array 150 is coupled to the switching network 60, via an input feed 34–41 and an output feed 42–49, respectfully. The switching network 60 selectively couples a predetermined transducer 152–166 to a drive line 170 and a signal line 172 in response to a select signal developed across a control line 174. It should be understood that the switching network 60 of the present invention can comprise any switching means known in the art, such as mechanical switching devices or electrical switching devices. It should be understood that in some configurations, the output feeds 42–49 and input feeds 34–41 can utilize the same feeds when Pulse-Echo Type time switching is incorporated or other similar techniques.

The switching network 60 of the present invention is coupled to the control system 70, via the drive line 170, the signal line 172, and the control line 174. Generally, the control system 70 is designed to "sequentially scan" each of the transducers 152–166 of the array 150 via a conventional sorting routine, and to compare the signals provided by the transducers 152–166. The control system 70 then drives the transducer providing the strongest signal, which measures the rate of blood flow through the selected blood vessel. It should be understood that any means for driving the transducers 152–166 and for comparing the signals provided by the transducers 152–166 falls within the scope of the invention. Further, any sorting routine known in the art can be employed.

Figure 4:
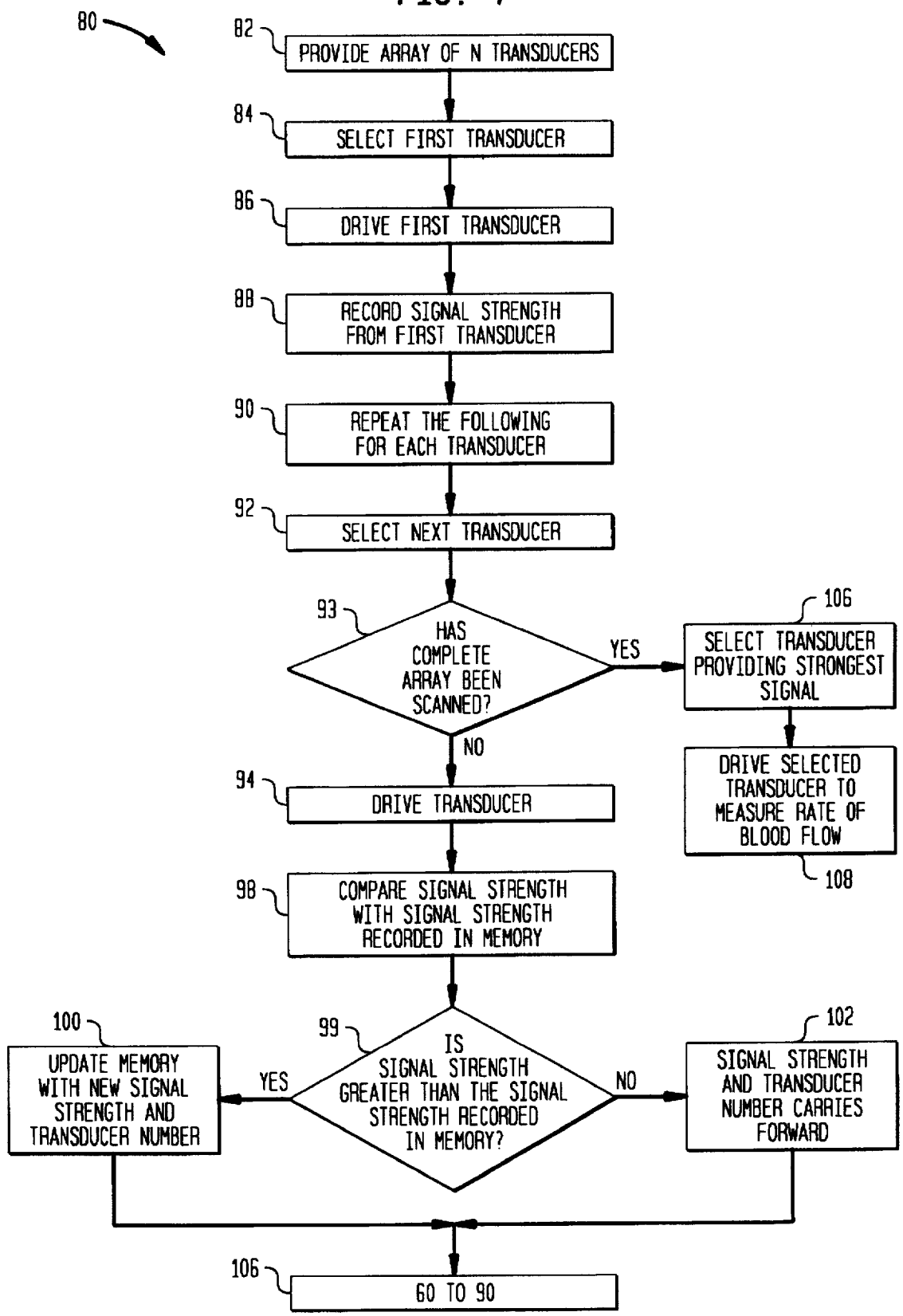
FIG. 4 is a schematic view of the "sequential scanning" procedure of the present invention.

Referring to FIG. 4, the "sequential scanning" procedure 80 is illustrated. An array of N number of transducers is provided (shown in box 82). Next, the control system 70 selects and drives the first transducer of the array (shown in boxes 84 and 86, respectively). The signal amplitude or "strength" provided by the transducer is then recorded in memory (shown in box 88).

The next set of steps is performed for each remaining transducer of the array (shown in boxes 90 and 104). First, the control system 70 selects and drives the next transducer of the array (shown in boxes 92 and 94, respectively). In between selecting the next transducer (box 92) and driving the transducer (box 94), the control system 70 checks to see if the complete array has been scanned (box 93). If it has, the control system 70 then advances to the step of box 106. If the complete array has not been scanned, the control system 70 then drives the next transducer (box 94).

The control system 70 then compares the strength of the signal provided by the selected transducer with the strength of the signal recorded in memory (shown in boxes 98 and 99). If the selected transducer provides a stronger signal then that recorded in memory, then the memory is updated with the stronger signal and the transducer is noted (shown in box 100). If the strength of the signal provided by the current transducer is less then that recorded in memory, then the signal recorded in memory is carried forward to be compared to the signal generated by the next transducer (shown in box 102). Accordingly, the strongest signal will be carried forward to the end of the procedure.

After the final transducer of the array is scanned, the control system 70 selects the transducer of the array which provided the strongest signal (shown in box 106). Finally, the selected transducer is driven by the control system 70 to measure the desired rate of blood flow (shown in box 108).

Such "sequential scanning" methods have proven useful in embodiments employing Doppler transducers where the Doppler pulse provides a strong signal-noise ratio signal. For example, the pulse time to reach a vessel and return, for vessels that are 1 cm deep, is about 13 microseconds (2 cm round-trip at 1.5 mm/microsecond). Thus, the total measurement and switch time per transducer is approximately 30 microseconds. For an exemplary embodiment comprising an array of 64 transducers, the complete array is measurable in 2 milliseconds, which is a short enough period of time for the blood flow to be considered constant. Therefore, the optimal transducer for measurement can be determined.

However, if the switching network 60 is not fast enough, or if the measured signal strength is so weak that it requires at least 50 pulses for a determination of the optimal transducer, then the "sequential scanning" procedure 80 may not be reliable. For example, in an exemplary embodiment comprising an array of 64 Doppler transducers, 0.1 seconds is required to scan all of the 64 transducers. Since the blood flow rate may change in this time period, "sequential scanning" would not be a reliable method. (It should be noted that the peak blood flow, occurring at systole, lasts less than a tenth of a second, and repeats at the pulse rate of about once per second). Further, although each transducer could be connected for an entire pulse period (1 second), 64 seconds of observation time would then be required to determine the optimal transducer.

In addition to the "sequential scanning" procedure 80 described herein, the control system 70 can be designed to perform a "sequential halving" procedure (perform a series of iterations until the transducer providing the strongest signal is determined).

Referring to FIG. 5, the "sequential halving" procedure 110 is illustrated. First, an array of N number of transducers is provided (shown in box 112). The array is then divided into two halves (shown in box 113). If a whole number remains (N is evenly dividable by 2), then the array is divided into a first half of N/2 transducers, from 1 to N/2, and a second half of N/2 transducers, from ((N/2)+1) to N (shown in boxes 114 and 115, respectively). However, if N is not evenly divisible by two, then the array is divided into a first half of ((N−1)/2) transducers, from 1 to ((N−1)/2), and a half section of ((N+1)/2) transducers, from ((N+1)/2) to N (shown in box 116).

At the end of this "halving" routine, the transducers in each of the halves are simultaneously scanned for an entire pulse period (shown in box 118). The control system 70 then compares the signals provided from each of the halves (shown in box 120). The half providing the strongest signal is then selected by the control system 70 (shown in box 122).

The "halving" procedure and scanning procedure is then repeated (shown in box 124) until the selected half comprises only one transducer, which is the transducer reporting the strongest signal. The selected transducer is then scanned (shown in box 126).

For arrays having a relatively large number of transducers, this "sequential halving" procedure 110 is substantially quicker than the "sequential scanning" procedure described above. For example, an array having 64 transducers will undergo 6 such halvings ($2^6$=64) to determine the optimal transducer. For the embodiment employing Doppler transducers, this amounts to a total of 12 seconds (at one second for each half, or two seconds per halving, times six), which is substantially less then the 64 seconds required by the "sequential scanning" method for connecting each of the 64 transducers for an entire pulse period of 1 second.

However, if the signal-noise ratio obtained using 64 Doppler transducers at a time is too low (because the 32 transducers are equivalent to a transducer much wider than the vessel, which as noted above reduces the signal-noise ratio), the control system 70 can be modified to perform a "hybrid" procedure, combining aspects of both the "sequential scanning" procedure 80 and the "sequential halving" procedure 110.

Referring to FIG. 6, the "hybrid" procedure 130 is illustrated. First, an array of N number of transducers is provided (shown in box 132). Next, the control system 70 divides the array into M sections, each section having N/M transducers (shown in box 134). For an embodiment having 64 transducers and for M being equal to four, the array is divided into four sections of sixteen transducers. Each of the sections are then scanned via the "sequential scanning" procedure 80 described herein to determine which section of the array provides the strongest signal (shown in box 136). The section providing the strongest signal is then selected by the control system 70 (shown in box 138) and undergoes the "sequential halving" procedure 110 described herein (shown in box 139). This procedure is repeated until the selected section comprises 1 transducer (shown in box 140). Finally, the remaining transducer is utilized to measure the desired blood flow rate (shown in box 142).

Although this "hybrid" procedure requires the same 12 seconds (4+2+2+2+2) as in the embodiment employing Doppler transducers via the sequential having method, it shows a 2:1 improvement in the signal-noise ratio as compared to the above "sequential scanning" procedure, because the noise, which is proportional to the number of transducers (i.e., The effective width of the transducer), is only half as great (16 versus 32).

While a single channel is assumed above, it is understood that one cab use more than one channel; if we divide or arrange the array into K segments for K channels, we can therefore perform K measurements simultaneously to determine which signal segment is strongest. While this approach involves additional circuitry and additional costs, it can be used to decrease the time needed to find the best segment. For example, if we have two channels, it takes only ½ the number of measurement periods, or if we have K channels for K transducers it takes less than one second.

Accordingly, the present invention provides an apparatus and method for quickly and without human intervention locating a blood vessel and for measuring the flow of blood through the located blood vessel. For example, the present invention can locate a blood vessel to be measured in substantially less time than many of the devices and methods of the prior art.

Additionally, the present invention provides an apparatus and method that measures the rate of blood flow through a blood vessel that comprises a plurality of transducers.

Further, the present invention provides an apparatus and method that measures the rate of blood flow through a blood vessel that comprises a plurality of Doppler transducers.

In addition, the present invention provides an apparatus and method that automatically determines the location of a blood vessel associated with a strong signal and measures the rate of blood flow through the blood vessel at the determined location.

Still further, the present invention provides an apparatus and method for automatically locating a blood vessel by sequentially scanning a plurality of transducers and comparing the signal strength provided by each of the transducers.

Finally, the present invention provides an apparatus and method for automatically determining the location of a blood vessel by performing a series of iterations on an array of transducers to determine the transducer that provides the strongest signal.

While the invention has been particularly shown and described with reference to preferred embodiments thereof, it will be understood by those skilled in the art that changes in form and details may be made therein without departing from the spirit and scope of the present invention.

What is claimed is:

1. An apparatus for locating a desired blood vessel within a predetermined volume of tissue, comprising:

a plurality of transducers operable to be positioned over the volume of tissue, wherein each said transducer when driven produces an output signal indicative of a characteristic of a blood vessel located under each said transducer; and control means for selectively driving said transducers in order to produce a plurality of output signals and for comparing said plurality of output signals in order to determine the said output signal having the largest amplitude which corresponds to said transducer positioned over the desired blood vessel.

2. The apparatus of claim 1, wherein said plurality of transducers are arranged in a configuration selected from a group consisting of a linear configuration and matrix configuration.

3. The apparatus of claim 1, wherein said plurality of transducers is a plurality of Doppler transducers including at least one flat surface.

4. The apparatus of claim 1, wherein the characteristic of the blood vessel is the blood flow rate.

5. The apparatus of claim 1, which further includes a switching network coupled between said plurality of transducers and said control means for selectively coupling each of said transducers to said control means.

6. The apparatus of claim 5, wherein said switching circuit is coupled to said control means by a drive line, a signal line and a control line.

7. The apparatus of claim 6, wherein each of said transducers are coupled to said switching circuit by an input feed and an output feed.

8. The apparatus of claim 6, wherein each of said transducers are coupled to said switching circuit by a single feed.

9. The apparatus of claim 1, wherein said switching circuit couples one of said transducers to both said drive line and said signal line in response to a select signal on said control line.

10. The apparatus of claim 1, wherein said control means further includes a memory device for storing said output signals.

11. The apparatus of claim 1, wherein said control means selectively drives said transducers in a sequential order.

12. The apparatus of claim 1, wherein said control means first selectively drives said transducers by first dividing said transducers into a predetermined number of sections and then sequentially driving each of said sections of transducers at a time until a desired section of transducers is chosen having output signals with the greatest amplitude and then said control means selectively drives said desired section of transducers by continually dividing said desired section of transducers into groups of halves and then sequentially driving each of said halves.

13. A method for locating a desired blood vessel within a predetermined scanning area of skin tissue, said method comprising the steps of:

positioning a plurality of transducers over the scanning area;

selectively driving said transducers in order to produce a plurality of output signals which are indicative of a characteristic of blood vessel located adjacently to said transducers; and comparing said plurality of output signals in order to determine said output signal having the largest amplitude which corresponds to said transducer positioned adjacent to the desired blood vessel.

14. The method of claim 13, which further includes driving said transducer positioned adjacent to the desired blood vessel after said comparing step in order to determine said characteristic of desired blood vessel.

15. The method of claim 13, wherein said selectively driving of said transducers is performed in a sequential order.

16. The method of claim 13, wherein said selectively driving of said transducers is performed by sequentially driving a quarter of said transducers at a time until said quarter of said transducers is chosen having output signals with the greatest amplitude.

17. The method of claim 13, wherein said selectively driving of said transducers is performed by continually dividing said transducers into groups of halves and then sequentially driving each of said halves.

18. The method of claim 13, wherein the characteristic of the blood vessel is the blood flow rate.

19. The method of claim 13, wherein said plurality of transducers are arranged in a configuration selected from a group consisting of a linear configuration and matrix configuration.

20. The method of claim 13, wherein said plurality of transducers is a plurality of Doppler transducers including at least one flat surface.

21. An apparatus for locating a desired blood vessel within a predetermined volume of tissue, comprising:

a plurality of transducers operable to be positioned over the volume of tissue, wherein each said transducer when driven produces an output signal indicative of a characteristic of a blood vessel located under each said transducer; and control means for selectively driving said transducers in order to produce a plurality of output signals and for comparing said plurality of output signals in order to determine the said output signal having the largest amplitude which corresponds to said transducer positioned over the desired blood vessel, wherein said control means selectively drives said transducers by continually dividing said transducers into groups of halves and then sequentially driving each of said halves.

* * * * *